(12) United States Patent
Dickey et al.

(10) Patent No.: US 6,381,488 B1
(45) Date of Patent: Apr. 30, 2002

(54) METHOD AND APPARATUS TO MEASURE THE DEPTH OF SKIN BURNS

(75) Inventors: Fred M. Dickey; Scott C. Holswade, both of Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 09/333,769

(22) Filed: Jun. 15, 1999

(51) Int. Cl.$^7$ .................................................. A61B 6/00
(52) U.S. Cl. ...................................................... 600/474
(58) Field of Search ................................. 600/310, 473, 600/474, 476, 477, 478, 475; 250/208.1, 330, 332, 334, 341.8

(56) References Cited

U.S. PATENT DOCUMENTS 5,747,789 A * 5/1998 Godik ........................ 600/310
5,865,167 A * 2/1999 Godik ........................ 600/310

* cited by examiner

*Primary Examiner*—George Manuel
(74) *Attorney, Agent, or Firm*—Brian W. Dodson

(57) ABSTRACT

A new device for measuring the depth of surface tissue burns based on the rate at which the skin temperature responds to a sudden differential temperature stimulus. This technique can be performed without physical contact with the burned tissue. In one implementation, time-dependent surface temperature data is taken from subsequent frames of a video signal from an infrared-sensitive video camera. When a thermal transient is created, e.g., by turning off a heat lamp directed at the skin surface, the following time-dependent surface temperature data can be used to determine the skin burn depth. Imaging and non-imaging versions of this device can be implemented, thereby enabling laboratory-quality skin burn depth imagers for hospitals as well as hand-held skin burn depth sensors the size of a small pocket flashlight for field use and triage.

22 Claims, 1 Drawing Sheet

METHOD AND APPARATUS TO MEASURE THE DEPTH OF SKIN BURNS

This invention was made with Government support under Contract DE-AC04-94DP85000 awarded by the U.S. Department of Energy. The Government has certain rights in the invention.

BACKGROUND

The present invention relates to early and non-invasive diagnosis of the depth and severity of skin burns. Such burns, when severe, are not only scarring and crippling, but also have been described as among the most painful injuries that a person can endure. Accurate estimation of the depth and severity of dermal burns would greatly add to the ability of the medical community to appropriately diagnose and treat such injuries.

Each year about two million Americans suffer serious burns. A large number of them require hospital treatment and 10,000–12,000 die from their injuries. Among those hospitalized, some 70,000 people require intensive care, and the cost of such treatment runs several hundred million dollars a year.

Serious burns are complex injuries. In addition to the burn injury itself, a number of other functions may be affected. Burn injuries can affect muscles, bones, nerves, and blood vessels. The respiratory system can be damaged, with possible airway obstruction, respiratory failure and respiratory arrest. Since burns injure the skin, they impair the body's normal fluid/electrolyte balance, body temperature, body thermal regulation, joint function, manual dexterity, and physical appearance. This damage often restricts the ability of the immune system to protect the burned area, resulting in extreme danger of infection and increasing the extent of permanent scarring. In addition to the physical damage caused by burns, patients also may suffer emotional and psychological problems that begin at the emergency scene and could last a long time.

Skin burns come in varying severity. The mildest, a first degree burn, is a superficial injury that involves only the epidermis or outer layer of skin. The skin is reddened and can be extremely painful, a sign that the nerves retain their function. Such a burn will heal on its own without scarring within two to five days. There may be peeling of the skin and some temporary discoloration.

More serious are second degree burns, in which the first layer of skin is charred through. The second layer, the dermal layer, is damaged in such a burn, but the burn does not pass through to underlying tissues. The skin appears moist and there will be deep intense pain, reddening, blisters and a mottled appearance to the skin. Second degree burns are considered minor if they involve less than 15 percent of the body surface in adults and less than 10 percent in children. When treated with reasonable care, second degree burns will heal themselves and produce very little scarring. Healing is usually complete within three weeks.

Third degree burns are the most severe, and involve all the layers of the skin. They are referred to as full thickness burns and are the most serious of all burns. These are usually charred black and include areas that are dry and white. While a third-degree burn may be very painful, some patients feel little or no pain because the nerve endings have been destroyed. This type of burn may require skin grafting. As third degree burns heal, dense crippling scars form.

The depth of a burn is the critical factor in the diagnosis and treatment of second and third degree burns. The most common treatment for moderate burns is to allow the natural sloughing of dead tissue, and then allow new skin to grow while protecting the burned region with moist bandages. In the case of burns serious enough that some thickness of dermis is actually destroyed, however, it can take as much as two weeks to determine if the residual dermis is capable of satisfactory regrowth, or if skin grafts must be carried out. The primary unknown here is the depth of the seriously damaged region. It is therefore important to be able to measure the extent of dead tissue soon after the burn occurs, and then to treat it promptly with the appropriate technique.

Previous methods to assess bulk depth were subjective and prone to error. Such methods have included, first and foremost, the detailed visual examination of an experienced medical practitioner. An early method to assess bulk depth is simply to biopsy the affected tissues. This invasive procedure, however, is painful, causes additional damage to already damaged tissues, and increases the very real danger of life-threatening infection.

A number of minimally invasive procedures to help in diagnosis of skin burns have been proposed, mostly aimed at detecting the amount of blood circulation remaining in the affected tissues. These include topical application of methylene blue, injection of fluorescein and its detection in the burned region by ultraviolet induced fluorescence, laser Doppler flowmetry, and fluorescence of intravenously injected indocyanine green dye. Such methods were found to be unable to accurately determine burn depth, and therefore have not enjoyed widespread acceptance in the medical community.

A NASA invention involved the use of ultrasound examination to estimate burn depth. When skin is burned, a constituent protein, collagen, becomes more dense. If there is an abrupt interface between burned and unburned tissues as depth is increased, this change of density produces a reflection of an input ultrasonic wave which can indicate burn density. Unfortunately, this interface is rarely abrupt, and hence the technique does not reliably measure burn depth. In addition, a sound transmission medium (typically an organic gel) is usually needed to couple the ultrasonic wave into the burned tissue. Such contamination of the burned tissue is contraindicated in virtually all treatment modalities. Accordingly, this technique has also met with little success (although it is FDA approved for burn diagnosis).

Several approaches to the use of characteristic thermal radiation from burned tissue have been proposed. Time-independent thermal imaging has been used in attempts to assess burn wounds. This approach is based on the assumption that (long wavelength) infrared emission from the skin is related to the amount of cutaneous blood flow in the surface of the wound. This assumption has been found to be wanting. The infrared emission from partial thickness burns is more closely related to heat sources in the underlying, unburned tissues than to the surface blood flow. In addition, such techniques suffer from variation of even normal skin temperature among the patient population, the cooling or heating effects of the immediate environment, the variability in emissivity of burned skin, and a number of other effects. Between the incorrect model and these uncharacterized biasing effects, such time-independent thermal imaging is rendered confusing at best and misleading at worst as an aid to burn diagnosis.

There is a need for improved diagnostic techniques for the depth of skin burns to accurately and quickly guide appropriate medical treatment. There is an additional need for such a technique to be minimally or non-invasive. Ideally, the apparatus for such a technique would be portable, rugged, and affordable, so as to be suitable for field triage and emergency room use.

SUMMARY

The present invention measures skin surface thermal relaxation time constants to determine skin burn depth. In one implementation, a thermal camera attached to a video recorder (or the digital equivalent, a frame buffer which converts a video signal to a string of digital data and a digital data recorder, such as a hard disk, magnetic tape, other mass memory devices, or random-access semiconductor memory) records the time-dependent response of the skin to heating or cooling by a small amount (typically a few degrees of temperature). The thermal stimulus can be delivered by a heat lamp, hot or cold air, or other means. Combining information from early and late thermal images reveals areas of the skin which return to equilibrium temperature at different rates, which correspond to different burn depths. As the time scale for return to equilibrium is typically less than a second, variation of external conditions during the examination do not generally affect this measurement technique.

DETAILED DESCRIPTION OF THE INVENTION

Figure 1:
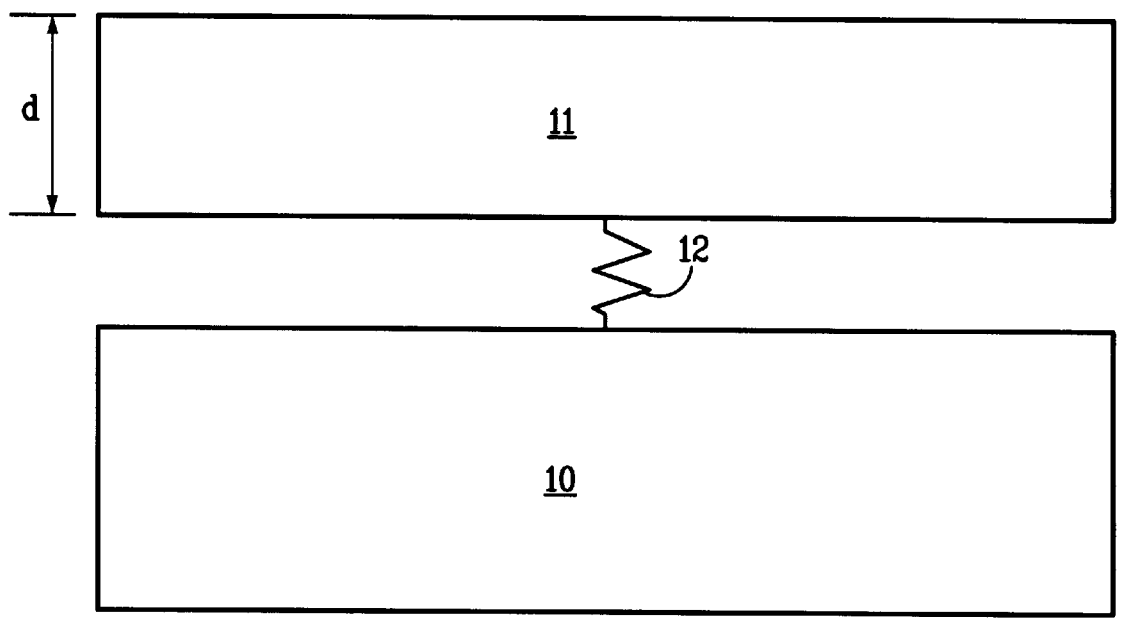
FIG. 1. Model for thermal response of burn ed skin layers.

To address the need for improved skin burn depth diagnostic techniques, Applicants have developed a new method for determination of the extent of damage in fresh skin burns, and a variety of apparatus suited to carrying out said method. The method involves measuring the rate at which the skin surface temperature relaxes after a thermal stimulus is applied.

The temperature of the surface of the skin depends on the subdermal body temperature, the temperature of the surrounding air, and the subdermal thermal conductance between the skin surface and the subdermal regions, which are warmed by blood circulation. As neither the subdermal body temperature nor the subdermal thermal conductance are known in the region of a burn, simply measuring the temperature of the skin surface, and even comparing to the temperature of an unburned region of skin, provides little reliable information concerning the extent of the burn.

Simple thermal imaging of a region of burned skin will also provide little useful information for diagnosis. A thermal camera images thermal radiation emanating from the skin surface. This radiation, which has peak intensity in the 8–12$\mu$ range, has a power density p per unit area of skin surface of $$\rho = \alpha \int_{8\mu}^{12\mu} \varepsilon(\lambda) \lambda^{-5} [\exp(hc/kT_s\lambda) - 1]^{-1} d\lambda$$

where $T_S$ is the skin surface temperature, $\alpha$ is a proportionality constant, $\varepsilon(\lambda)$ is the emissivity of the skin surface as a function of the radiated wavelength $\lambda$, h is Planck's constant, c is the speed of light, and k is Boltzmann's constant.

When integrated over all possible wavelengths, and the assumption of constant emissivity is made, the above expression reduces to the well-known Stefan-Boltzmann $T^4$ dependence of thermal radiation power on the temperature of the emitting body. Any real apparatus, however, examines only a particular region of the electromagnetic spectrum in obtaining a "thermal image". In the present demonstrations, a thermal camera sensitive to optical wavelengths between 8 and 12 microns was used.

On evaluating the amount of thermal radiation emitted by a surface near 310° K. (body temperature) integrated over the 8–12$\mu$ wavelength range, under assumption of constant emissivity over that wavelength range, the dependence of this integrated power on body temperature is found to closely approximate a $T^4$ law. That is, the integrated power is very nearly proportional to $T^4$. In the absence of dramatic variations in emissivity or in thermal camera sensitivity over this range of wavelengths, the measured thermal radiation power over the 8–12$\mu$ wavelength range can be approximated as proportional to the temperature of the body being observed to the fourth power.

In the present invention, time constant parameters characterizing the rate at which the skin surface temperature $T_S$ relaxes back to an equilibrium value following a temporary heating or cooling event are measured by comparing successive images from a thermal camera. The upper layers of severely burned skin lose most or all of their blood circulation, with the depth of this circulation-free region depending on the severity of the burn.

In a simple model of heat flow (see FIG. 1), a layer of burned tissue 11 with depth d lays atop a substratum of relatively healthy tissue 10, which remains at or near a nominal body temperature. In the model, the layer of burned tissue 11 is thermally isolated from the substratum of healthy tissue 10 save for the action of a thermal link 12. For a given burn depth d, the thermal mass of the layer of burned tissue 10 is proportional to d, and the average thermal conductance between the severely burned region and the (relatively) healthy underlying tissues, which is closely related to the thermal conductance of the thermal link 12, will also be roughly proportional to d.

The result is that the skin surface temperature will relax exponentially toward an equilibrium skin surface temperature with a time constant $\tau$ roughly proportional to $d^2$. That is, following a temperature excursion of $\Delta T$ (caused, e.g., by a pulse of light incident on the skin which disappears at t=0), the skin temperature will relax according to $$T_S(t) = T_S(0) - \Delta T(1 - e^{-t/\tau}).$$

Measuring this time constant $\tau$ thus reveals the depth of the skin burn. Based on known values for the thermal conductivity of the burned skin layers, the skin temperature relaxation time constant $\tau$ for a burn depth of 100 $\mu$m is roughly 30 milliseconds, whereas for a burn depth of 300 $\mu$m $\tau$ is roughly 290 milliseconds, in reasonable agreement with the expected $d^2$ dependence.

What is actually measured in a thermal imaging camera is the power of thermal radiation emitted by pixels making up a given region of skin surface. A common type of thermal camera takes frames at periodic time intervals $\delta t$. Also, it will often be impossible to synchronize a real apparatus sufficiently that a thermal image is taken exactly at t=0. As a result, there will be a constant time shift $\gamma$—that is, the thermal images will be taken at discrete times n$\delta t$+$\gamma$.

Using the $T^4$ power dependence discussed earlier, the thermal radiation power at the times that the thermal images are taken is simply $$P_n = \xi[T_S(0) - \Delta T(1 - e^{(n\delta t + \gamma)/\tau})]^4.$$

This relation has 5 unknown parameters, $\xi$, $T_S(0)$, $\Delta T$, $\gamma$, and $\tau$. In principle, the data from 5 separate (not necessarily sequential) thermal imaging frames will allow extraction of the thermal relaxation time constant $\tau$. In practice, quantization errors, statistical fluctuations, and system noise suggest that more complex data reduction, such as least-squares curve fitting, should be used to obtain a more reliable value for the time constant $\tau$, a value based on more than 5 data points. Such techniques are well-known in the art.

Note that the system of 5 equations in 5 unknowns which results when 5 data points are taken at known time intervals can be solved by a digital computer in the conventional manner, but can also be computed by an analog computer with no need for digital computation. This can be done if the signal from the thermal radiation sensor is converted into a stream of analog data, and then four or more time-delayed streams of equal magnitude are generated therefrom. These five streams of data then, at any single time, represent five time-separated thermal radiation intensity values. These values define the set of five equations needed to calculate the skin burn depth. If the thermal radiation sensor provides a scanned image of the skin surface, then the time delays associated with the time-delayed streams must be integral multiples of the time between successive video frames, so that the five thermal radiation intensity values all correspond to the same region of the skin surface. The non-imaging version of this technique can be especially useful in small portable burn depth meters.

Although the thermal flow model above is a reasonable approximation to the behavior of burned skin, actual burns show reasonably small, but significant, variations from the predicted behavior. Rather than developing more complex models, for which many parameters will be unknown in practice, it is more appropriate to correct the simple model described above based on a database obtained by studying actual and well-characterized burns with the method of the present invention. Methods for carrying out such corrections are again well-known in the art.

Figure 2:
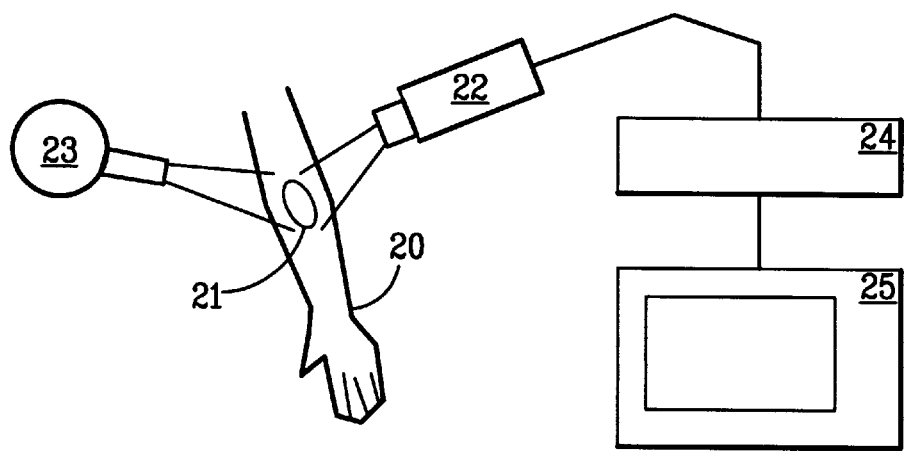
FIG. 2. Schematic illustration of a skin burn thickness measurement apparatus according to the present invention.

One implementation of the apparatus to carry out the new method is shown in FIG. 2. A portion of a patient's body (here an arm 20) containing a burned area 21 is positioned so that the focal region of a thermal camera 22 and the output of a transient thermal source 23 can simultaneously be directed toward said burned area 21. The output of the thermal camera is analyzed by processor 24, which carries out an analysis of the type described above, and the results are displayed on the display 25.

The thermal camera 22 preferably should be capable of discriminating temperature differences smaller than 1° K., with time intervals between measurements generally less than 0.1 seconds. In fact, common frame rates for thermal cameras are 30 and 60 frames per second. As an alternative to evenly spaced thermal image measurements, the thermal camera can be triggered when desired. Note that the change in power for a variation in skin surface temperature of ~5° K. is about 5%. As a result, the combined system and statistical noise of thermal camera 22 must be well below 1% of the expected thermal radiation, and still better should be below 0.1%.

In principle, these temperature changes could alternately be monitored by techniques which make contact with the skin, e.g., thermocouples, liquid crystals, etc. However, touching serious burns always carries along a major risk of causing infection in the immunocompromised burn tissue. Appropriate caution must therefore be used whenever contact is made with the burned area. In addition, such contact is difficult to make without altering the skin surface temperature. Finally, obtaining good thermal contact with the burned skin can be difficult. Despite such difficulties, such temperature detection methods can have useful applications.

Commercial thermal imaging cameras sensitive in the 8–12$\mu$ wavelength range are readily available, and can be used for this purpose. Note that the present invention can also be implemented in a simplified version where a simple nonimaging detector provides general information about a small skin area. This implementation, which will be discussed in more detail below, is well suited to small, easily portable burn depth monitors. Such could be extremely useful, e.g., for triage in mass accidents involving fire or explosion.

The role of the transient thermal source 23 is to raise or lower the temperature of the skin area exposed to the thermal camera 22 by a small amount, typically less than a few °K., and then to quickly remove the influence which is changing the skin temperature. ('Quickly' here means within a time period on the order of, or preferably substantially less than, the characteristic timescale for skin temperature relaxation, which in healthy skin is generally less than 10 milliseconds.)

Such a thermal stimulus can be applied by a variety of means, but attention should be paid to the possibility of infection. Thermal stimulus methods should preferably be chosen with a view to interact as benignly as possible with the burned tissue. These combined requirements suggest use of an optical source, e.g., an electrically powered heat lamp or a photoflash lamp. Such a lamp can easily produce the required increase in skin temperature, can be gated on and off rapidly, by electrical or mechanical means, and does not transfer any matter to the burned skin. So long as the optical pulse used for testing is not intense enough to damage the skin, such a stimulus is not expected to adversely affect either burned or normal skin regions.

Another approach to providing the needed thermal stimulus is to blow a jet of hot or cold gas across the burned area. The jet can be controlled by a valve capable of quickly cutting off the flow of gas. Heat can be provided chemically or electrically to a jet of any pressurized gas. Similar techniques can be used to cool a pressurized gas, but it will usually be simpler to cool the gas by allowing the gas to expand, or by generating the gas from a pressurized liquefied gas, such as butane. Careful design is required in all cases to avoid heating or cooling the skin so much that additional damage occurs. It is also necessary to design a delivery device which substantially evenly distributes the heated or cooled gas to the test area. The gas used, of course, must be chosen to be benign in contact with normal and burned skin, and should be sterile or nearly so when it makes such contact. All of these requirements can easily be encompassed by current heat gun or aerosol canister technology.

Other approaches exist (e.g., topical application and subsequent evaporation of a volatile liquid to the skin being tested), but these tend to be more invasive and carry additional danger of causing infection or other damage to the burned skin.

Finally, the skin burn depth, once obtained by processing the data from the thermal radiation sensor, must be provided as output useful to the operator. In the case of a non-imaging sensor, this output might be a single digital number activating a display, such as an LED or LCD array or a printer. Alternatively the output can be an analog parameter, such as voltage, linked to a meter. When an imaging sensor is used, the output can take the form of tables of data (e.g., burn depth data vs position on the skin surface), but such data is easiest to understand if presented as an image, where the skin burn depth is represented by a visual parameter of the image. Some visual parameters which can be used include intensity, contrast, and/or color parameters such as hue, tint, and saturation. Additional graphics constructed from the data, such as contour lines of equal burn depth, can also allow easy interpretation of the burn depth information.

The above description of the present invention has concentrated on particular implementations of the invention in order to point out the essential features of the invention. This is not intended to limit the scope of the invention, which scope is to be set only by the appended claims.

What is claimed is:

1. An apparatus to measure burn depth on mammalian skin, comprising:

a) a thermal transient generator directed to a skin surface; and b) means for measuring the rate at which the skin surface temperature relaxes after a thermal stimulus has been applied by the thermal transient generator and obtaining a measure of the extent of burn depth therefrom.

2. The apparatus of claim 1, wherein said means includes a sensor directed to the skin surface to detect thermal transients in the skin surface.

3. The apparatus of claim 1, wherein the sensor detects the average thermal radiation intensity of the skin surface.

4. The apparatus of claim 3, wherein the sensor comprises an infrared detector.

5. The apparatus of claim 4, wherein the infrared detector is sensitive to thermal radiation in the 8–12 $\mu$m range.

6. The apparatus of claim 4, wherein the infrared detector comprises a photodiode.

7. The apparatus of claim 4, wherein the infrared detector comprises a bolometer.

8. The apparatus of claim 7, wherein said bolometer is a superconducting thin-film bolometer.

9. The apparatus of claim 1, wherein the sensor detects variations in thermal radiation intensity over the skin surface and reports such variations as thermal radiation data, and the data processor calculates spatial variation of the skin burn depth over the skin surface from the stored thermal radiation data.

10. The apparatus of claim 9, wherein the sensor is a thermal camera.

11. The apparatus of claim 10, wherein the thermal camera is sensitive to thermal radiation in the 8–12 $\mu$m range.

12. The apparatus of claim 9, further comprising a display which exhibits an image of the skin surface, such that a visual parameter of said image conveys information about the skin burn depth.

13. The apparatus of claim 12, wherein said visual parameter is chosen from the group consisting of intensity, hue, tint, contrast, equi-burn depth lines, and combinations thereof.

14. The apparatus of claim 2, wherein said means includes a data recorder for recording the thermal transient as a function of time.

15. The apparatus of claim 1, wherein said data recorder stores the thermal radiation data from said sensor at a series of predetermined times.

16. The apparatus of claim 1, wherein said data recorder stores the thermal radiation data from said sensor at predetermined and substantially constant time intervals.

17. The apparatus of claim 1, wherein said thermal transient generator comprises a heat lamp directed onto the skin surface and an electrical switch controlling the function of the heat lamp.

18. The apparatus of claim 1, wherein said thermal transient generator comprises a heat lamp directed onto the skin surface and an optical switch functionally positioned between the heat lamp and the skin surface.

19. The apparatus of claim 1, wherein said thermal transient generator comprises a flash lamp directed onto the skin surface.

20. The apparatus of claim 1, wherein said thermal transient generator comprises a hot air generator, a hot air jet which directs a stream of hot air onto the skin region, and a valve to turn the hot air jet on and off.

21. The apparatus of claim 1, wherein said thermal transient generator comprises a cold air generator, a cold air jet directed onto the skin region, and a valve to turn the cold air jet on and off.

22. The apparatus of claim 1, wherein said thermal transient generator comprises a laser directed onto the skin surface.

* * * * *